(12) United States Patent
Migneco et al.

(10) Patent No.: US 10,836,403 B2
(45) Date of Patent: Nov. 17, 2020

(54) DISTRACTEDNESS SENSING SYSTEM

(71) Applicant: Lear Corporation, Southfield, MI (US)

(72) Inventors: Francesco Migneco, Saline, MI (US); Arjun Yetukuri, Rochester Hills, MI (US); David Gallagher, Sterling Heights, MI (US); Jasmine Pizana, Scottville, MI (US)

(73) Assignee: LEAR CORPORATION, Southfield, MI (US)

( * ) Notice: Subject to any disclaimer, the term of this patent is extended or adjusted under 35 U.S.C. 154(b) by 272 days.

(21) Appl. No.: 15/830,892

(22) Filed: Dec. 4, 2017

(65) Prior Publication Data

US 2019/0168771 A1 Jun. 6, 2019

(51) Int. Cl.
*A61B 5/00* (2006.01)
*G06K 9/00* (2006.01)
(Continued)

(52) U.S. Cl.
CPC ......... *B60W 50/085* (2013.01); *A61B 5/4064* (2013.01); *B60W 30/09* (2013.01);
(Continued)

(58) Field of Classification Search
CPC . B60W 2040/0818; B60W 2040/0827; B60W 2040/0836; B60W 2040/0845;
(Continued)

(56) References Cited

U.S. PATENT DOCUMENTS 5,694,939 A 12/1997 Cowings
5,807,114 A 9/1998 Hodges et al.
(Continued)

FOREIGN PATENT DOCUMENTS

CN 204147427 U 2/2015
DE 10126224 A1 12/2002
(Continued)

OTHER PUBLICATIONS

Stout, Cynthia S., et al., Increasing Accuracy in the Assessment of Motion Sickness: A Construct Methodology, Ames Research Center, NASA Technical Memorandum 108797, Dec. 1993, Moffett Field, California.
(Continued)

*Primary Examiner* — Todd Melton
(74) *Attorney, Agent, or Firm* — Brooks Kushman P.C.

(57) ABSTRACT

A distraction detection system includes using a first signal, e.g., EDP signals or vehicle speed, and an additional signal to determine whether a person is distracted. The distraction system can be part of a vehicle seating system, A vehicle seating system is described and includes a seat configured to support an occupant and to be mounted in a vehicle and occupant sensing system at least partially integrated into the seat to sense an occupant. The sensing system senses a first criterion with respect to the occupant. A controller is configured to receive the first criterion signal from the sensing system and a second criterion to determine a distraction state of the driver. The controller can also determine a false distraction state using the distraction state and other criterion in a vehicle. The controller outputs a control signal when the distraction state exceeds a distraction threshold and when distraction is confirmed.

20 Claims, 5 Drawing Sheets

(51) Int. Cl.
*B60W 50/08* (2020.01)
*B60W 30/09* (2012.01)
*B60W 50/14* (2020.01)
*B60W 50/16* (2020.01)

(52) U.S. Cl.
CPC ............ *B60W 50/14* (2013.01); *B60W 50/16* (2013.01); *G06K 9/00845* (2013.01); *B60W 2050/143* (2013.01); *B60W 2520/10* (2013.01); *B60W 2540/26* (2013.01); *B60W 2554/00* (2020.02)

(58) Field of Classification Search
CPC .. B60W 2040/0863; B60W 2040/0872; G06K 9/00845; A61B 5/4064; G06F 3/015
See application file for complete search history.

(56) References Cited

U.S. PATENT DOCUMENTS

| | | | |
|---|---|---|---|
| 6,366,207 | B1 | 4/2002 | Murphy |
| 6,438,399 | B1 | 8/2002 | Kurth |
| 7,138,922 | B2 | 11/2006 | Strumolo et al. |
| 7,437,219 | B2 | 10/2008 | Bos |
| 7,774,052 | B2 | 8/2010 | Burton et al. |
| 8,698,639 | B2 | 4/2014 | Fung et al. |
| 8,903,494 | B2 | 12/2014 | Goldwasser et al. |
| 9,002,458 | B2 | 4/2015 | Pal et al. |
| 9,014,811 | B2 | 4/2015 | Pal et al. |
| 9,124,955 | B2 | 9/2015 | Geva et al. |
| 9,135,803 | B1 | 9/2015 | Fields et al. |
| 9,149,236 | B2 | 10/2015 | Chun et al. |
| 9,233,244 | B2 | 1/2016 | Pal et al. |
| 9,272,689 | B2 | 3/2016 | Fung et al. |
| 9,298,985 | B2 | 3/2016 | Krueger |
| 9,302,584 | B2 | 4/2016 | Walsh et al. |
| 9,389,595 | B2 | 7/2016 | Caskey et al. |
| 9,440,646 | B2 | 9/2016 | Fung et al. |
| 9,454,887 | B1 | 9/2016 | Matalgah |
| 9,460,601 | B2 | 10/2016 | Mimar |
| 9,463,794 | B1 | 10/2016 | Silver et al. |
| 9,475,502 | B2 | 10/2016 | Fung et al. |
| 9,536,411 | B2 | 1/2017 | Foley et al. |
| 9,539,944 | B2 | 1/2017 | Tzirkel-Hancock et al. |
| 9,712,736 | B2 | 7/2017 | Kearns et al. |
| 9,956,963 | B2 | 5/2018 | Vijaya Kumar et al. |
| 10,054,443 | B1 | 8/2018 | Patel et al. |
| 10,210,409 | B1 | 2/2019 | Migneco et al. |
| 10,379,535 | B2 | 8/2019 | Migneco et al. |
| 10,425,459 | B2 | 9/2019 | Rider et al. |
| 2006/0015000 | A1 | 1/2006 | Kim |
| 2007/0156295 | A1 | 7/2007 | Stephane |
| 2009/0174573 | A1 | 7/2009 | Smith |
| 2009/0268022 | A1 | 10/2009 | Omi |
| 2012/0116198 | A1 | 5/2012 | Veen et al. |
| 2012/0150430 | A1 | 6/2012 | French et al. |
| 2012/0259181 | A1 | 10/2012 | Fujita et al. |
| 2012/0265262 | A1 | 10/2012 | Osorio |
| 2012/0330173 | A1 | 12/2012 | Park et al. |
| 2013/0204153 | A1 | 8/2013 | Buzhardt |
| 2013/0325202 | A1 | 12/2013 | Howard et al. |
| 2014/0136450 | A1 | 5/2014 | Lee |
| 2014/0139655 | A1 | 5/2014 | Mimar |
| 2015/0032382 | A1 | 1/2015 | Lee et al. |
| 2015/0245777 | A1 | 9/2015 | Della Torre et al. |
| 2015/0313475 | A1 | 11/2015 | Benson et al. |
| 2015/0328985 | A1 | 11/2015 | Kim et al. |
| 2015/0360608 | A1 | 12/2015 | Tzirkel-Hancock et al. |
| 2015/0379362 | A1 | 12/2015 | Calmes et al. |
| 2016/0001781 | A1 | 1/2016 | Fung et al. |
| 2016/0090097 | A1 | 3/2016 | Grube et al. |
| 2016/0133151 | A1 | 5/2016 | O'Dowd et al. |
| 2016/0260343 | A1 | 9/2016 | Resl |
| 2016/0285938 | A1 | 9/2016 | Rider et al. |
| 2016/0292988 | A1* | 10/2016 | McCleary ............. G08B 21/14 |
| 2016/0354027 | A1 | 12/2016 | Benson et al. |
| 2017/0068245 | A1 | 3/2017 | Scofield et al. |
| 2017/0071525 | A1 | 3/2017 | Lin et al. |
| 2017/0083757 | A1* | 3/2017 | Enomoto ............... G06F 3/011 |
| 2017/0136842 | A1 | 5/2017 | Anderson et al. |
| 2017/0188927 | A1 | 7/2017 | Nakashima et al. |
| 2017/0196497 | A1 | 7/2017 | Ray et al. |
| 2017/0267170 | A1 | 9/2017 | Be et al. |
| 2017/0278122 | A1 | 9/2017 | Kaehler |
| 2017/0311831 | A1* | 11/2017 | Freer .................. A61B 5/04014 |
| 2017/0351812 | A1 | 12/2017 | Green et al. |
| 2017/0355377 | A1 | 12/2017 | Vijaya Kumar et al. |
| 2017/0360363 | A1 | 12/2017 | Fonseca et al. |
| 2017/0367635 | A1 | 12/2017 | Hur et al. |
| 2017/0367651 | A1 | 12/2017 | Tzvieli |
| 2017/0370732 | A1 | 12/2017 | Bender et al. |
| 2018/0008145 | A1 | 1/2018 | Freer et al. |
| 2018/0136191 | A1 | 5/2018 | Asvadi et al. |
| 2018/0143006 | A1 | 5/2018 | White |
| 2018/0189681 | A1 | 7/2018 | Harrivel et al. |
| 2018/0197636 | A1 | 7/2018 | Firminger et al. |
| 2018/0229674 | A1 | 8/2018 | Heinrich et al. |
| 2018/0276362 | A1 | 9/2018 | Baughman et al. |
| 2019/0049968 | A1 | 2/2019 | Dean et al. |
| 2019/0087691 | A1 | 3/2019 | Jelveh |
| 2019/0108407 | A1* | 4/2019 | Okayasu ............. G06F 16/5866 |
| 2019/0133511 | A1 | 5/2019 | Migneco et al. |
| 2019/0176837 | A1 | 6/2019 | Williams et al. |
| 2019/0332902 | A1 | 10/2019 | Gallagher et al. |
| 2019/0373038 | A1 | 12/2019 | Rider et al. |
| 2019/0373114 | A1 | 12/2019 | Gullander |
| 2020/0012403 | A1 | 1/2020 | Sculley et al. |

FOREIGN PATENT DOCUMENTS

| | | |
|---|---|---|
| DE | 102012002037 B4 | 3/2015 |
| EP | 2308559 A2 | 4/2011 |
| FR | 2880166 A1 | 6/2006 |
| JP | 2010241963 A | 10/2010 |
| JP | 2017021651 A | 1/2017 |
| WO | 2007090896 A1 | 8/2007 |

OTHER PUBLICATIONS

Migneco, Francesco et al., Amendment Under 37 C.F.R. § 1.111 for U.S. Appl. No. 15/808,325, filed with the U.S. Patent and Trademark Office on Jan. 9, 2020 (10 Pages).

Gallagher, David et al, Preliminary Amendment for U.S. Appl. No. 15/963,697, filed with the U.S. Patent and Trademark Office on Jan. 15, 2020 (8 Pages).

Burgess, M., "This car headrest monitors your brain waves to stop you falling asleep at the wheel", WIRED Online Article, Jan. 15, 2017, 9 pgs.

Lisetti, C., "Affective Intelligent Car Interfaces with Emotion Recognition", In Proceedings of 11th International Conference on Human Computer Interaction, Las Vegas, NV, USA, Jul. 2005.

Wess, J., "Prototype Testing of EEG Headrests", Freer Logic Online Article—Comments Off on Prototype Testing of EEG Headrests, Aug. 3, 2017, 2 pgs.

Gallagher, David et al., Supplemental Amendment Under 37 C.F.R. § 1.111 for U.S. Appl. No. 51/963,697 filed with the U.S. Patent and Trademark Office on Jun. 2, 2020 (12 Pages).

Migneco, Francesco et al., Amendment Under 37 C.F.R. § 1.111 for U.S. Appl. No. 15/808,325 filed with the U.S. Patent and Trademark Office dated Jul. 10, 2020 (10 Pages).

Gallagher, David, et al., Amendment Under 37 C.F.R. §1.116 for U.S. Appl. No. 15/963,697 filed with the U.S. Patent and Trademark Office dated Sep. 8, 2020 (8 pages).

* cited by examiner

| | INPUT FROM PRIMARY SENSOR | | INPUT FROM SECONDARY SENSOR | | | | |
|---|---|---|---|---|---|---|---|
| | EDP WRT DEFINED RANGE | EXAMPLE ANALYSIS: BASED ON EDP ONLY | VEH SPEED WRT SURROUNDING VEHICLES | GPS | OUTWARD CAMERA | INWARD CAMERA | CORRECTED ANALYSIS W/SENSOR FUSION BASED ON INPUTS FROM REMAINING SENSORS/EDP | WAS THE ANALYSIS BASED ON FIRST INPUT A FALSE ALARM? | COUNTER-MEASURE REQUIRED? |
| 401 | NORMAL | FOCUSED | ABNORMAL | NO TRAFFIC CONGESTION | NO TRAFFIC CONGESTION | NORMAL | FOCUSED | NO | NO |
| 402 | NORMAL | FOCUSED | ABNORMAL | NO TRAFFIC CONGESTION | NO TRAFFIC CONGESTION | ABNORMAL | NOT FOCUSED | YES | YES |
| 403 | ABNORMAL | NOT FOCUSED | ABNORMAL | NO TRAFFIC CONGESTION | NO TRAFFIC CONGESTION | ABNORMAL | NOT FOCUSED | NO | YES |
| 404 | ABNORMAL | NOT FOCUSED | NORMAL | TRAFFIC CONGESTION | TRAFFIC CONGESTION | NORMAL | FOCUSED | YES | NO |
| 405 | ABNORMAL | NOT FOCUSED | NORMAL | TRAFFIC CONGESTION | TRAFFIC CONGESTION | ABNORMAL | NOT FOCUSED | NO | YES |

*FIG. 4*

DISTRACTEDNESS SENSING SYSTEM

TECHNICAL FIELD

The present disclosure relates to systems with integrated sensors to provide sensed information about a person's distracted state.

BACKGROUND

It is advantageous to be able to detect a person's focus and attention. For instance, driving a motor vehicle while distracted, which is a type of driver error, is a significant cause of preventable road accidents. Vehicle systems that assist in warning a driver of distracted driving or take action in such an occurrence may reduce the number of such accidents or attempt to mitigate damage caused by driver distractedness.

SUMMARY

Systems and methods for detecting distractedness or lack of focus are described. The system may include an electro-dermal potential (EDP) sensing system at least partially integrated into the vehicle cabin, which can include the a singular configuration or combined configuration involving the vehicle seat, headliner, structural pillars, instrument panels, and steering wheel, to sense a person and configured to output an electro-dermal potential signal; at least one additional sensor to sense additional data that can be used to determine distractedness; and a controller to receive the electro-dermal potential signal from the electro-dermal potential sensing system and the vehicle sensor to determine a distraction state of the person using both the electro-dermal potential signal and the vehicle-related data to reduce the likelihood of a false distraction state using only one of the vehicle-related data or the electro-dermal potential signal, the controller is to output a control signal when the distraction state is identified or exceeds a distraction threshold. In an example embodiment, the system can also determine when there is or is not a false distraction.

In an example embodiment, the controller is configured to determine a false distraction state based in both the vehicle-related data and the electro-dermal potential signal.

In an example embodiment, the control signal is to adjust operation of an adaptive braking system in the vehicle.

In an example embodiment, the system includes a seat configured to support the person as an occupant and to be mounted in a vehicle; and wherein the electro-dermal potential sensing system includes a contactless sensor mounted in the seat adjacent a head of the occupant.

A vehicle seating system with sensors to sense the distraction of a driver or occupant of the vehicle who may be seated in a vehicle seat. The seat may be configured to support an occupant and to be mounted in a vehicle. An electro-dermal potential sensing system is at least partially integrated into the seat to sense physiological properties of an occupant, e.g., a driver, and configured to output an electro-dermal potential signal. The sensed physiological properties of the occupant can include brain cortical activity. A controller is positioned in the vehicle to receive the electro-dermal potential signal from the electro-dermal potential sensing system to determine a distraction state of the driver. The controller also determines a false distraction state using the distraction state and other sensor signals in a vehicle, the controller is to output a control signal when the distraction state exceeds a distraction threshold and when there is not a false distraction determined.

In an example embodiment, the control signal is to adjust operation of a collision avoidance system or an adaptive braking system in the vehicle.

In an example embodiment, the electro-dermal potential system includes a plurality of contactless sensors mounted in the vehicle cabin.

In an example embodiment, the seat includes a head rest. The plurality of contactless sensors includes one or more headrest sensors mounted in the headrest to measure electro-dermal potential at a head of the driver.

In an example embodiment, the seat includes a driver warning device to indicate to the driver that the control signal is output from the controller.

In an example embodiment, the controller measures driver distraction based on individual frequency components, or rations thereof, in the electro-dermal potential signal.

In an example embodiment, the controller uses the electro-dermal potential signal as an input to determine driver distraction and when distraction is detected outputs the control signal to increase a time to impact variable in an object avoidance calculation.

In an example embodiment, the sensor signals include a video output from a cabin camera to detect the driver. The controller can use the video output and the electro-dermal potential signal to determine the distraction state of the driver.

In an example embodiment, the sensor signals include a navigational position signal from a navigational position sensor to detect position of the vehicle. The controller can use the navigational position signal and the electro-dermal potential signal to determine if there is a false distraction state of the driver.

In an example embodiment, the sensor signals include an external camera signal from an outward facing imager to produce video external to the vehicle. The controller can use the external camera signal and the electro-dermal potential signal to determine the false distraction state of the driver.

In an example embodiment, the sensor signals include an internal video signal, an external camera signal, a navigational position signal, and a vehicle speed signal. The controller can use the internal video signal, the external camera signal, the navigational position signal, the vehicle speed signal and the electro-dermal potential signal to determine a possible false distraction state of the driver or to correct the distraction state by any number of countermeasures.

A vehicle system is described that includes a vehicle safety sensor system configured to sense external objects around the vehicle and output an external sensor signal. The vehicle system may also include a seat configured to support an occupant and to be mounted in a vehicle and an electro-dermal potential system at least partially integrated into the seat and configured to output an electro-dermal potential signal. The electro-dermal potential system includes a plurality of contactless sensors mounted in the vehicle. A controller is to receive the electro-dermal potential signal from the electro-dermal potential system and the external sensor signal and to output a control signal, using the electro-dermal potential signal and the external sensor signal, to adjust operation of the vehicle safety sensor system in the vehicle.

In an example embodiment, the vehicle safety sensor system includes a detection and ranging system with a range setting to sense objects outside including a position and a range of an external object, e.g., a natural obstacle, another vehicle, an animal, or a person, and the external sensor signal includes the position and range of the external object.

In an example embodiment, the controller outputs a range extension signal when the controller determines that the driver is distracted or lacking in focus on driving a vehicle using the electro-dermal potential signal, and wherein the vehicle safety system extends the range setting when the controller outputs the range extension signal.

In an example embodiment, the vehicle safety sensor system includes a light sensor, a LIDAR, a camera, or combinations thereof.

In an example embodiment, the vehicle safety sensor system includes a radio frequency sensor, RADAR or both.

In an example embodiment, the vehicle system includes a collision avoidance system having a trigger time based on the control signal from the controller. The collision avoidance system is configured to trigger an avoidance action based on the trigger time In an example embodiment, the collision avoidance system has a first trigger time when distraction is not detected and a second trigger time when distraction is detected. The second trigger time being less than the first trigger time.

A vehicle system is described that uses at least two sensors sensing two criteria, which are different, when processed by a controller produces an indication of distractedness or focus of the occupant or driver. In an example, a first sensor senses a first criterion relating to distracted driving and controlled by the driver. In an example, a second sensor senses a second criterion relating to distracted driving and representing an environmental condition not controlled by the driver. A controller receives the first criterion and the second criterion and determines a relative relationship between the first criterion and the second criterion with the relative relationship exceeding a distractedness threshold to indicate distracted driving.

In an example, the first criterion is vehicle speed and the second criterion is traffic congestion, other vehicles speeds adjacent the vehicle, or a combination of both. In an example, the controller compares the vehicle speed relative to the second criterion, and when the vehicle speed slows relative to the second criterion, the controller will indicate distractedness of the driver.

Any of the above examples may be combined with each other to form additional embodiments of the present disclosure.

BRIEF DESCRIPTION OF THE DRAWINGS

FIG. 4 is a chart of false distraction detection according to an example embodiment.

DETAILED DESCRIPTION

Figure 1:
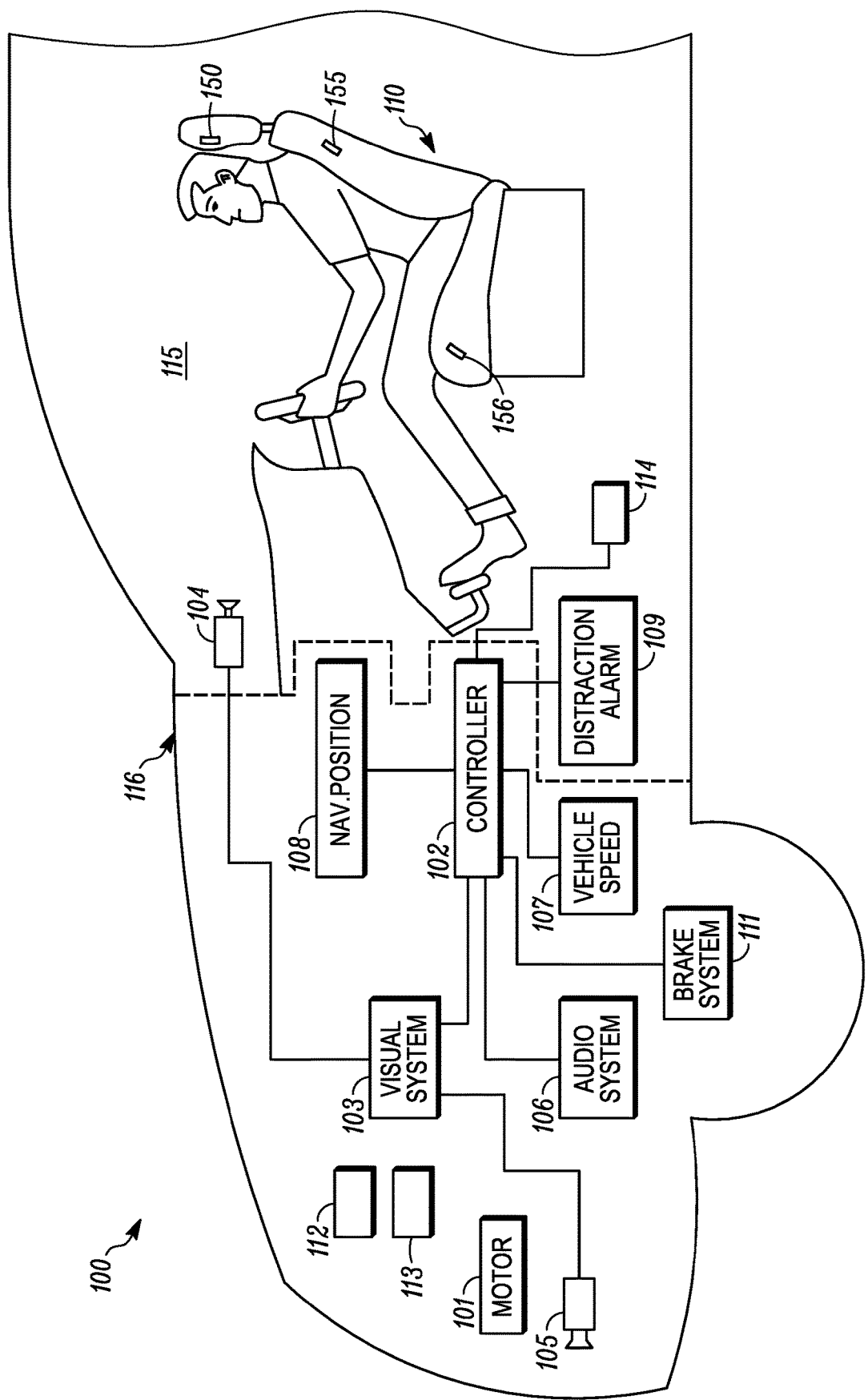
FIG. 1 is a schematic view of a vehicle according to an example embodiment.

As required, detailed embodiments of the present invention are disclosed herein; however, it is to be understood that the disclosed embodiments are merely exemplary of the invention that may be embodied in various and alternative forms. The figures are not necessarily to scale; some features may be exaggerated or minimized to show details of particular components. Therefore, specific structural and functional details disclosed herein are not to be interpreted as limiting, but merely as a representative basis for teaching one skilled in the art to variously employ the present invention.

The present disclosure is generally directed to vehicle mounted sensors that can be embedded at least partially in the vehicle cabin or in any part of the foam, trim, headrest, frame or a combination thereof of a vehicle seat. The sensors can also be positioned in the headliner, the instrument panel, structural pillars, the steering wheel, or combinations thereof. At least one of the sensors determines the electro-dermal potential originating primarily from brain cortical activity. Such EDP sensing can be contact or non-contact (e.g., field sensing) and can also sense muscle activity and skin characteristics. This will reveal high-level central nervous system (CNS) functions such as distraction or drowsiness. The systems described herein employ real-time processing of the electrical potential fluctuations, e.g., comparing various frequency bands of the sensed signal with respect to each other. These can act as the primary brain activity quantitative classifiers. The present systems may use the sensed signals along with other sensor information to determine false positives of distraction based on the sensed EDP signal. This system, through the acquisition of the appropriate physiological metrics and use of a software algorithm, can determine if the occupant is distracted and not attentive to the mad task of the moment while correcting for false positive indications of distraction.

A distractedness sensing system can be integrated with the seat including one or more sensors embedded in any part of the seat, e.g., the foam, the trim, the headrest or a combination thereof. The contactless EDP sensing system can be supplemented by appropriate physiological metrics [heart rate, heart rate variability (HRV), Cardiorespiratory Coupling/Synchrogram (CRS), breathing rate, EDP pattern shift and the like, for both standard and complex non-linear dynamics] of the seat occupant, e.g., the driver. A controller can receive the sensed physiological metrics relevant signals and determine if the occupant is distracted and therefore if attention and reaction time is affected. The controller can be adapted to individual occupants using an automated user-specific calibration.

This system can also include cameras strategically positioned to look at the driver. Inward cameras can be used in conjunction with the seat sensors to achieve sensor fusion and increase specificity and accuracy of the distraction level detection. The camera generates multiple images of the occupant, which can be analyzed to determine additional occupant metrics. The metrics can include head position, a blink rate, pupil dilation, eye position, fixation, gaze patterns, eyelid closure, head movement facial expression, overall skeletal position, and the like. The camera system takes an image and image processing circuitry analyzes the image to determine the image metric.

The use of various metrics from different sources provides an objective quantification of distraction of the occupant. The distraction quantification can be combined with other data in the vehicle to prevent false indications of distraction, e.g., vehicle performance, driving environment, and the like. If the distraction quantification level exceeds a distraction threshold, then the vehicle may automatically trigger countermeasures, e.g., alerts, alarms, collision avoidance, and the like. If the distraction status of the driver is quantified, the vehicle can change reaction times of the collision avoidance system, e.g., the adaptive braking system, to optimize the response of the system itself in view of the driver condition as at least partly determined by the distraction level.

A vehicle system is described that uses at least two sensors sensing two criteria, which are different, when processed by a controller produces an indication of distractedness or focus of the occupant or driver. In an example, a first sensor senses a first criterion relating to distracted driving and controlled by the driver. In an example, a second sensor senses a second criterion relating to distracted driving and representing an environmental condition not controlled by the driver. A controller receives the first criterion and the second criterion and determines a relative relationship between the first criterion and the second criterion with the relative relationship exceeding a distractedness threshold to indicate distracted driving.

FIG. 1 shows a vehicle 100 including a cabin 115 and an engine bay 116, which can be forward of the cabin 115. The engine bay 116 houses a motor 101 that provides motive power to the vehicle. A controller 102 includes an electrical signal processor adapted to execute tasks, which can be stored in a memory. The tasks can process sensed signals according to rules loaded into the controller 102. The sensed data can be stored in memory associated with the controller 102.

Visual systems 103 are provided to receive instructions from the controller 102 and produce visual displays in the vehicle, e.g., in the cabin on display screens, the dashboard, a mobile electronic device associated with the vehicle. The displays produced by the visual systems can be images sensed by an internal camera 104, an external camera 105, collision warnings, distraction warnings, and the like. The visual system 103 can process the image data from the cameras 104, 105 before providing the image data to the controller 102. The visual system 103 can process images to identify objects and the position of the driver in an example embodiment. This data can be provided to the controller 102.

An audio system 106 can be part of a head unit in the vehicle. The head unit can be an electronic processor to process audio signals or sensed signals in the vehicle. The audio system 106 can sense audio in the cabin 115 and output audio into the cabin, e.g., using multiple speakers. The audio output from the audio system 106 can be warnings as described herein based on instruction from the controller 102. The audio warnings can be spoken words or tones to indicate driver distraction, change in settings, imminent danger, activation of collision warning system or combinations thereof.

A vehicle speed sensor 107 is provided to detect the speed of the vehicle and provide a speed signal to the controller 102. The vehicle speed sensor can include the throttle position sensor.

A navigational position system 108 detects the position of the vehicle by receipt of satellite signals or ground based position signals. The navigational position system 108 can include a global navigation satellite system (GNSS) such as Global Positioning System (GPS), Beidou, COMPASS, Galileo, GLONASS, Indian Regional Navigational Satellite System (IRNSS), or QZSS. The navigational system can include a receiver that receives differential correction signals in North American from the FAA's WAAS system. The navigational position system 108 provides accurate position of the vehicle to the controller 102.

A distraction alarm 109 is positioned in the cabin 115. The distraction alarm 109 can include mechanical alarms like vibration devices that can be positioned in the steering wheel or the seat. The distraction alarm 109 can be a signal to vibrate a mobile electronic device associated with the vehicle and a passenger in the vehicle.

A vehicle seat 110 is positioned in the cabin 115 and is configured to support a person, e.g., a driver or a passenger. The seat 110 can include a plurality of sensors 150, 155, 156 to detect various biometric characteristics of the person. The sensors 150 can be contactless and can sense EDP adjacent the head of the seated person. The sensors 155 and 156 can detect other biometric information. The sensors 155, 156 can be contactless, e.g., sensing parameters from the occupant without physically contacting the occupant. In some instances, at least one of the sensors 156 can contact the occupant.

A brake system 111 is provided to brake the wheels of the vehicle. The brake system 111 can be activated by the driver and can also be activated automatically by the controller 102, e.g., when distracted driving is detected, a crash is detected as imminent, or an imminent danger is detected as described herein.

A laser sensing system 112, e.g., a LIDAR, is provided. The laser sensing system 112 emits light in pulses and detects the light returned after the light reflects of object external to the vehicle 100. The laser sensing system 112 can produce a digital three-dimensional representation of the external environment around the vehicle in the direction of the light pulses. The laser sensing system 112 can perform laser scanning to produce a representation around the vehicle. The external environment can include other vehicles, signs, animals, people, and other objects. The representation or individually identified objects can be provided to the controller 102 for use in the vehicle as described herein.

A RADAR sensing system 113 is provided in the vehicle. The RADAR sensing system 113 emits radio frequency energy pulses and detects the returned pulses to identify objects around the vehicle or map the external environment. The representation or individually identified objects can be provided to the controller 102 for use in the vehicle as described herein.

Other typical vehicle systems may be included in the vehicle 100 but are not illustrated for clarity of the drawings. The controller 102 may provide inputs to these other systems.

Figure 2:
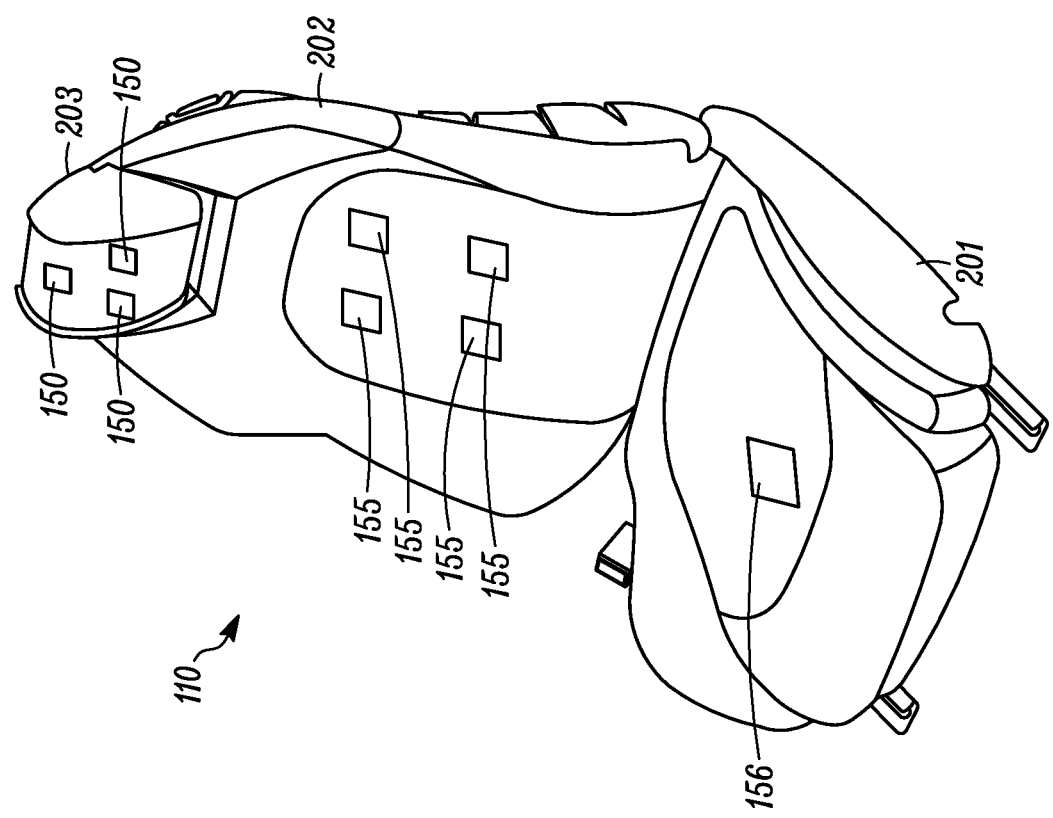
FIG. 2 is a schematic view of a vehicle seat with sensors therein according to an example embodiment.

FIG. 2 shows the vehicle seat 110 configured to be fixed in a cabin of a motor vehicle. The seat 110 is adapted to support a person on a base 201 in an upright position against a seat back 202. The base 201 is fixed to the floors in the vehicle cabin, e.g., by rails. A headrestraint 203 may be positioned at the top of the seat back and act as a headrest. Each of the base 201, seat back 202, and headrestraint 203 include a rigid frame, comfort layers on the frame and an external covering. A plurality of sensors 150, 155, 156 can be supported in the seat. A plurality of first sensors 150 may be positioned in the headrest 203 and adapted to sense EDP signals from the occupant of the seat 110. A plurality of second sensors 155 may be positioned in the seat back 202. The plurality of second sensors 155 may also sense EDP signals from the seated occupant. The plurality of second sensors 155 may include at least one sensor that does not sense EDP signals. One or more third sensors 156 are positioned in the seat base 201. The third sensors 156 may also sense EDP signals. The plurality of second sensors 155 may include at least one sensor that does not sense EDP signals and may, e.g., sense presence of a person in the seat using sensors in the seat back or seat and sense weight of the occupant of the seat using sensors in the seat base. The sensors 150 develop raw EDP signals, which are filtered to produce analysis signals including frequency components relevant to the EDP of the person in the seat while attenuating unrelated frequency components.

In another aspect, a method is provided for monitoring a mental state of a person having a body including a head positioned at the headrestraint adjacent sensors in the headrestraint. The method also includes positioning a sensor at least proximate to portions of the skin of the body below the head to develop raw signals, and processing the raw signals to produce at least one bandpass-filtered state-indicating signal representative of raw signal magnitude within a predetermined frequency range as an indication of the mental state (e.g., distracted state) of the person.

At least one sensor 150 is positioned to be at the posterior of the head near or at the occipital-visual cortical region. This may assist in accurately measuring brain waves, e.g., through EDP. As driving is a visually dominant cognitive task the ability to detect processing in that anatomical area of the brain (e.g., the visual cortex) as well as other processing and cognitive networks of mental processing offers the ability to monitor visual attention level specifically. For example, visual habituation is the brain's ability to decrease its response to repeated stimuli once the information has been processed and is no longer perceived as a relevant processing demand. In addition to generally low visual attention, the occupant should not experience significant habituation patterns as the visual scenery though mundane at times is in continuous variation and the conditions demand attention in such areas. Lack of activity related to visual processing or habituation of visual stimuli can serve as a subset classification of potential distraction in addition to other brain wave responses and secondary monitoring systems.

Figure 3A:
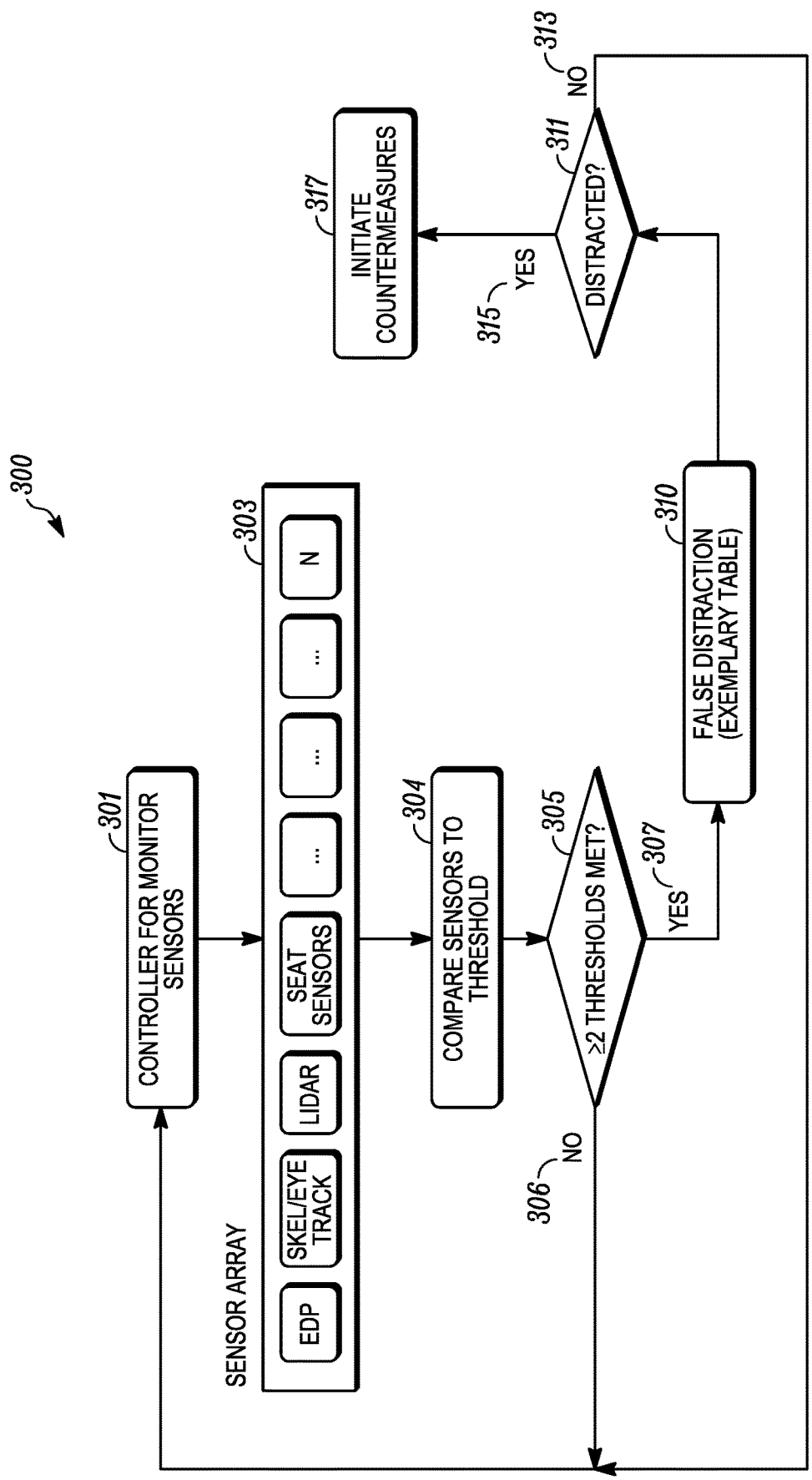
FIG. 3A is a functional block diagram of a vehicle system according to an example embodiment.

FIG. 3A shows schematic view of a process 300 that can be implemented to determine distractedness using sensors, e.g., in a vehicle 100. At 301, the controller monitors sensed data from an array of sensors 303 associated with the vehicle. The sensors can be any of the sensors described herein. Examples of sensors in the sensor array 303 include the EDP sensor, internal and external imagers, laser based sensors, seat sensors, and the like. The sensor array can include up to N sensors, where N is any positive integer.

The sensor array 303 can monitor a driver or an occupant of the vehicle seat. The monitoring can include EDP sensing using the contactless sensors 150. The EDP signals are used to detect a distraction state of the driver. The EDP signals can be separated into various sub-signals, e.g., at different frequencies, by using filters to allow certain divisions into sub-bands. These sub-bands may overlap in frequency ranges. A general range of frequencies for each sub-band can be defined within a reasonable variance. A first sub-signal can be up to four hertz. A second sub-signal can be four hertz to seven hertz. A third sub-signal can be seven hertz to fourteen hertz. A fourth sub-signal can be fourteen hertz to about thirty hertz. A fifth sub-signal can be about thirty hertz to about one hundred hertz. Other sub-signals may overlap these ranges for the first through sixth sub-signals, e.g., from eight hertz to thirteen hertz. The relationships between these sub-signals can be used to determine whether the driver is distracted from the task of driving. The patterns of the sub-signals or the ratios of multiple sub-signals to each other can be used to determine if a distraction is occurring.

The sensor array 303 can include a vehicle cabin imager, e.g., a camera, that is used to detect the driver in the vehicle seat. The camera data is used to detect a distraction pattern in the driver. The camera can detect movement or lack of movement of the driver, facial features of the driver or both. The camera data can be video signals sent to a data processor in the controller to determine if the driver matches a distraction pattern. The data processor can determine if the actions of the driver or the image of the driver matches a known distraction pattern. Examples of distraction patterns can include head position or eye position not directed forward in a manner of a driver looking out the windshield.

The sensor array 303 can include external imagers, cameras, LIDAR (LIght Detection and Ranging), RADAR (RAdio Detection and Ranging), and SONAR (SOund Navigation and Ranging). These systems can detect objects around the vehicle, e.g., other vehicles, stop signs, stop lights, and the like. The imagers can detect the color and shape of external objects. LIDAR and RADAR can detect the size and position of external objects relative to the vehicle, which may be in motion.

At 304, the sensed data from each of the individual sensors are compared to thresholds for sensed data of the respective sensors. The image data from an imager is compared to image data, e.g., the change in pixels can be used to indicate that a threshold in the image data has been exceeded. The EDP data can be compared at multiple frequencies to determine if an EDP signal, e.g., a brain wave, exceeds an EDP threshold to indicate distractedness. The EDP data can also be compared to EDP patterns over a time period with these patterns being indicative of a person who is focused or a person who is distracted. A LIDAR, RADAR, or sonar sensor can detect the relative position of the vehicle compared to objects or other vehicles. A navigational sensor can be used to determine the location of the vehicle and provide speed data for the present vehicle and other vehicles around the present vehicle being operated by the person for whom distractedness is being determined. Seat sensors can determine the position of the person, metabolic and physiological parameters, biometric parameters, EDP, and other data related to the person. Each of the sensed data can be compared to thresholds that are stored in memory in the vehicle. The memory is associated with the vehicle controller.

At 305, it is determined if at least two or more of the sensed data exceeds a distractedness threshold. The process 300 relies on distractedness being determined based on at least data from two sensors. The primary sensor can be the EDP sensor, which can be weighted more heavily in the process to control the vehicle. If only one sensor indicates distractedness, then the process moves to step 306 and returns to monitoring at step 301. If two or more sensors indicate distractedness via triggered thresholds, then it is determined if whether the determination of distractedness is false at step 310. In an example, the EDP data from the EDP sensor by itself may falsely indicate distractedness. The other data can be combined with the EDP data or sensor results to determine if the EDP is falsely indicating distractedness or that the person is focused on a different task. An example of a process for determining falseness is described in greater detail with regard to FIG. 4.

At step 311, the combined data from the sensor array determines whether the driver is distracted by using the results from two or more sensors or using all of the results from each sensor. If distractedness is determined at step 315, then the vehicle can initiate countermeasures at step 317. If distractedness is not found, i.e., the person is focused, then the process moves to step 313 and returns to the controller monitoring the sensors 301. The countermeasures at step 317 can include a distraction warning, e.g., an audible warning through the vehicle audio system, a light warning, or mechanical warnings. Mechanical warnings can include vibration warnings, e.g., in the steering wheel, in the seat, in pedals, in the driver's mobile phone, or combinations thereof. The mechanical warnings can vibrate vehicle components that contact the occupant or would notify the occupant. The driver's mobile phone may be electrically connected to the vehicle through a wired connection or wireless connection, e.g., Bluetooth, WIFI or the like. The countermeasures can also include secondary countermeasures, e.g., activating and/or increasing the range of the vehicle anti-collision systems or adaptive cruise control. The secondary countermeasures are vehicle controls and processes. Primary countermeasures are those that encourage the distracted occupant to refocus and not be distracted.

In an example embodiment, the LIDAR/RADAR detection range can be increased as a countermeasure. The external camera range can be increased. Increasing the range of detection allows the systems to detect objects farther away from the vehicle and allows more time to automatically process to compensate for the distracted state of the driver. The increase of the time buffers representing the distance from the vehicle to an object outside the vehicle, e.g., other vehicles on the road, road hazards and the like increases the distance from an object at which the vehicle can automatically activate a countermeasure or detect the object. The increase of the time buffers reduces the time to impact from the vehicle to the object. The vehicle will then activate collision avoidance systems sooner when the driver is distracted. After step 317, the process can return to step 301.

Figure 3B:
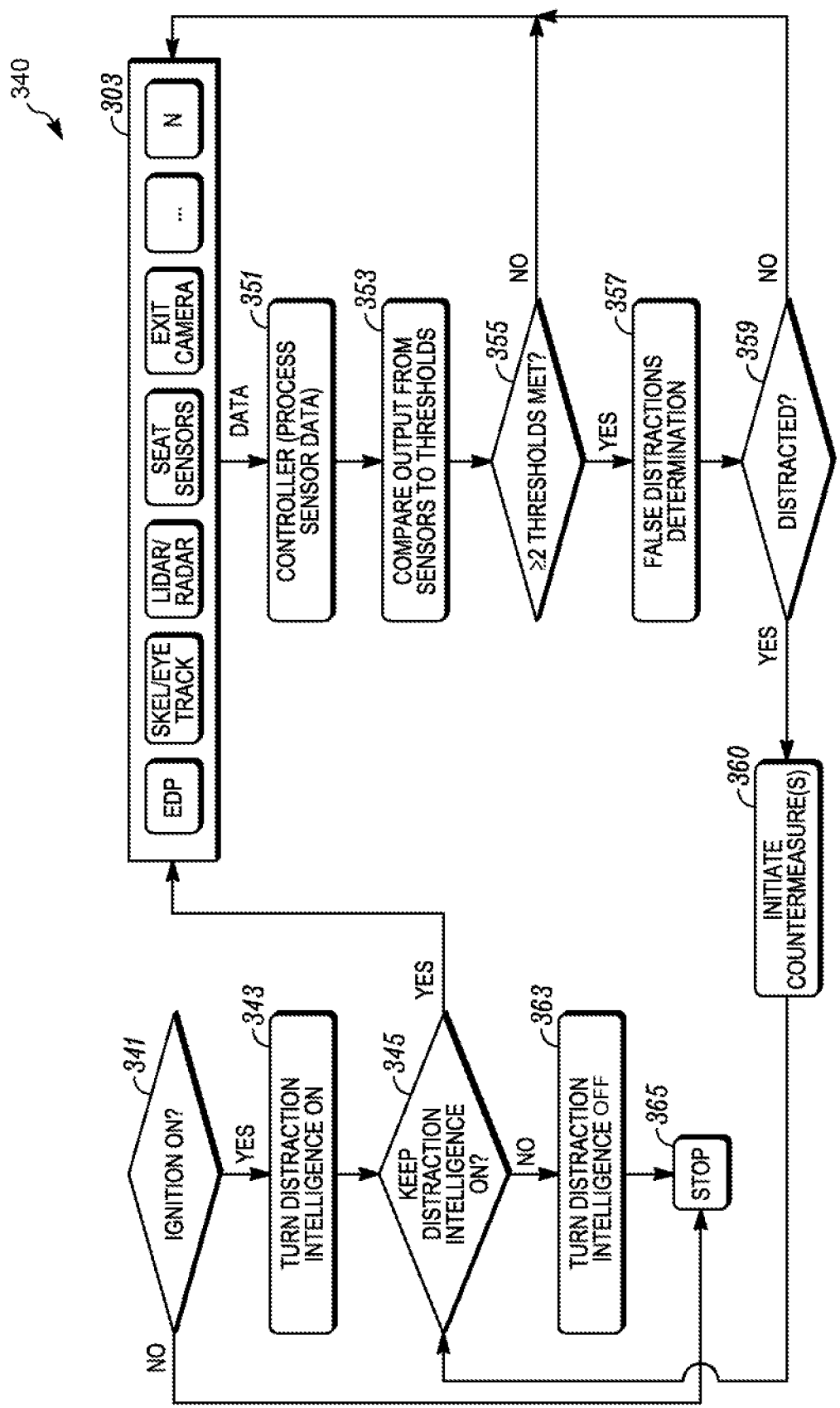
FIG. 3B is a functional block diagram of a vehicle system according to an example embodiment.

FIG. 3B shows process 340 that can be implemented in the vehicle 100 to sense a distracted state of the occupant of the seat. At step 341, it is determined if the vehicle is on, e.g., by determining that the ignition is in an "ON" state. If the vehicle is off then, the process 340 ends at step 365. If the vehicle is ON, then the vehicle turns on its system for detecting distractedness by loading instructions in the controller circuitry. In an example embodiment, turning in the distracted detection in the vehicle can be optional, e.g., set in a setting procedure or turned OFF by a switch. In an example, when the vehicle turns ON, it also initiates the vehicle intelligence system. At step 345, the driver of the vehicle has the option to manually turn off the system for detecting distractedness. If the driver chooses to turn off the system for detecting distractedness at step 345, the system turns OFF at step 363. The process 340 can also be turned OFF when the vehicle is not moving or in park for a period of time. The decision to keep the system for detecting distractedness ON can be based on receiving at least two or more sensor signals that can be used to determine distractedness. In an example, at least one of the two sensor signals can be the EDP signal.

With the distraction process 340 remaining ON at step 345, the process moves to activating the sensor array at step 303. The sensor array can be the same sensor array as described with reference to FIG. 3A and may include any sensor as described herein. The sensor array at step 303 outputs sensed data to the controller 102 to process the sensed data at step 351. The processing at step 351 can include filtering or normalizing the raw data from the sensors in the sensors array from step 303. The sensed data from step 351 is compared to thresholds that are individualized for each type of sensor data. If two or more thresholds are not met at 355, which indicate the person is focused, then the process returns to the sensor array sensing data at step 303. The present process is based on the assumption that the occupant is not distracted. It will be understood that a similar process, which assumes the driver is distracted and the system must prove the occupant is not distracted, is within the scope of the present disclosure.

It will be understood that the sensing of data at step 303 can be continuous with the return indicating the present data does not indicate distractedness. If two or more different thresholds are met, then the process moves to a false alarm determination at step 357. If a false distractedness is determined, the vehicle may not trigger countermeasures. In an example, the navigation positioning (e.g., GPS) data is used to confirm the distraction determination based on the EDP signal distractedness determination. In an example, the vehicle speed data is used to confirm the distraction determination. In an example, the images from the inward camera, the outward camera or both are used to confirm the distraction determination.

At step 359, a final determination of distractedness is made, which takes into account the sensor data relied on to determine distractedness and the false distracted determination to reduce the likelihood of false distractedness determinations. If it is determined at step 359 that the person is not distracted, then the process returns to step 303. If distractedness is determined, then the vehicle can initiate countermeasures at step 360. After countermeasures are initiated, then process returns to a determination to keep the distraction algorithm ON at step 345. The countermeasures can remain ON for a set period of time or until the system determines that the occupant is no longer distracted or when the distractedness is determined to be false. In an example embodiment, the countermeasures remain ON until the present methods and systems determine that the driver is now not distracted.

The present distractedness determination processes 300, 340 use data from two or more different sensors to determine distractedness. The EDP sensor can provide the primary data but data from other vehicle sensors can be combined to more accurately determine distractedness. The other sensed data can be data related to the occupant within the vehicle cabin, data from outside the vehicle cabin, or both. The combination of the distractedness determination based on each individual sensor can be used to reduce the likelihood of false indications of distractedness.

In an example embodiment, the step 343 of turning ON the distraction intelligence in the vehicle proceeds to the sensors 303 for YES and to step 363 when the intelligence is turned OFF. The keep intelligence ON step 345 can be between the initiate countermeasures step 360 and the sensors 303.

FIG. 4 shows a table 400 of various sample scenarios 401-405 to use multiple inputs from different sources to determine the state of distractedness of a person. Any one sensor can be used as the primary data. Any other sensor can be used as secondary data to correct, to validate, or to invalidate the determination of distractedness based on the primary sensed data. For example, as shown in FIG. 4, the sensed EDP data can be the primary input for determining distractedness of a person being sensed by the sensors as described herein. The sensors for primary data can include vehicle speed, relative vehicle speed, positional data, navigational data, outward camera data, inward facing camera, and the like. The addition of the secondary data can be used to correct for false indications of driver distraction based solely on the primary data. The inputs for secondary data can include vehicle speed, navigational positioning information (GPS in North America), an external facing camera, an inward facing camera, possibly focused on the driver, and the like. The data from these devices is used in controller circuitry to determine if there is a false indication of driver distraction.

In first scenario 401 using the sensors as described herein, the first sensed signals from the EDP sensor are determined to be normal, i.e. within a defined tolerance or range. The output from the controller circuitry will indicate that the diver is focused. A focused status of an occupant is the occupant person being not distracted from the task of driving. Thus, the primary sensor system first determines that the person is not distracted. Then the secondary sensor data can be added to verify driver's state of distraction. The vehicle speed with respect to the surrounding traffic as a secondary input is judged to be abnormal. The vehicle speed from the current vehicle is known from on board sensors. The surrounding vehicle speeds can be determined from sonar, radar, or lidar sensors, or combinations thereof, on the vehicle. The surrounding vehicle speeds can also be transmitted between vehicles in a vehicle communication network. Here, the relative vehicle speed is abnormal, i.e. outside a defined tolerance or expected range. An additional secondary sensor signal is the navigational position data with regard to a vehicle and possible traffic congestion at the vehicle location. The navigational or vehicle positioning sensor (e.g., GPS in North America) is not sensing any traffic congestion in the sample embodiment. Traffic congestion can be a measure of vehicle position over time relative to the normal overall traffic flow for a particular time of day. This data can include the position of the present vehicle and combined with amalgamated data from a server with regard to traffic at that location and that time of day. Traffic congestion can also be sensed by an outward facing sensor, e.g., an imaging sensor, a camera sensor, a RADAR sensor, a laser sensor, or a sonar sensor. Here the outward sensor is a camera or imaging sensor and it does not detect traffic congestion. The inward imager or camera senses that the occupant is normal. The corrected distracted analysis based on a fusion of the primary sensed data and the secondary sensed data results in the determination from the controller circuitry that the occupant is focused, i.e. not distracted. A counter measure to counter act the distractedness of the occupant is not triggered.

In the second scenario 402, the sensed EDP is normal i.e. within a defined tolerance or range and the analysis based on the primary sensor data is that the occupant is focused. The secondary sensors can be used to check or confirm the primary sensor analysis. The relative vehicle speed is abnormal. The navigational result is no traffic congestion. The outward imaging sensor shows no traffic congestion. The inward camera senses abnormal occupant behavior, i.e. outside of a defined tolerance or range. The corrected analysis of the primary sensor data combined with the secondary sensor data results in a determination the occupant is distracted. The system further determines that the primary sensor data was analyzed and reached a false result. This can be used to teach the algorithm that its result was incorrect. The algorithm in the controller circuitry for analyzing the primary sensor data can change its parameters to more closely match the corrected results from the corrected analysis. The system can use the corrected analysis of not focused to trigger counter measures as described herein.

In scenarios 403-405, the primary sensor determines that the EDP sensed data is abnormal in the sense that the occupant is not focused or is distracted. The EDP sensed data can be compared to focused waveforms and unfocused waveforms in the controller circuitry. When outside the focused thresholds of variability from the focused waveform, then the controller circuitry can determine that the occupant is not focused and therefore distracted. The secondary sensed data from the secondary sensors can be used to correct the determination that the occupant is distracted.

In the third scenario 403, the secondary sensors provide additional data to be used with the primary abnormal determination from the primary sensor. The relative vehicle speed is abnormal. The navigational system sensor determines that there is no traffic congestion. The outward imager determines that there is no traffic congestion. The inward imager provides data showing abnormal, which indicates that the occupant is distracted. The primary data or analysis is combined with the secondary data (one input or more than one output) and determines that the occupant of the seat is not focused on the task of driving, i.e. is distracted. The analysis from the first sensor input is confirmed or does not produce a false distractedness reading or alarm. The countermeasures in the vehicle can be triggered based on the primary analysis and the sensor fusion with the secondary sensed data. The countermeasures can be any countermeasure as described herein.

In the fourth scenario 404, the secondary sensors provide additional data to be used with the primary abnormal determination from the primary sensor. The relative vehicle speed is normal. The navigational system sensor determines that there is traffic congestion. The outward imager determines that there is traffic congestion. The inward imager provides data showing normal, which indicates that the occupant is focused. The primary data or analysis is combined with the secondary data and determines that the occupant of the seat is focused. The analysis from the first sensor input is determined to be a false reading that the driver is distracted. The secondary sensor data corrects the incorrect or false alarm from the primary sensor analysis. The countermeasures in the vehicle are not triggered.

In the fifth scenario 405, the secondary sensors provide additional data to be used with the primary abnormal determination from the primary sensor. The relative vehicle speed is normal. The navigational system sensor determines that there is traffic congestion. The outward imager determines that there is traffic congestion. The inward imager provides data showing abnormal, which indicates that the occupant is distracted. The primary data or analysis is combined with the secondary data and determines that the occupant of the seat is not focused, i.e. is distracted. The analysis from the first sensor input is confirmed or does not produce a false distractedness reading or alarm. The countermeasures in the vehicle can be triggered based on the primary analysis and the sensor fusion with the secondary sensed data. The countermeasures can be any countermeasure as described herein.

The scenarios 401-405 represent an example of circuitry applying an algorithm to the sensed data to output a resulting signal to trigger an alert, vehicle control, or vehicle countermeasure in attempt to lessen the effects of the distracted driving. Circuitry may exploit artificial intelligence and neural networks to determine distractedness and/or false distractedness.

The criteria from the secondary sensors, e.g., as shown in FIG. 4, can be used in some example embodiments to indicate distractedness. The secondary sensors can detect secondary criteria related to the occupant or driver within the vehicle cabin. The secondary criteria can also include sensed data related to the environment outside the vehicle. The sensed data can be used to derive the secondary criteria. Relative relationships between criteria sensed by the secondary sensors can be determined and when these relationships indicate distractedness, the vehicle can warn the occupant or alter operation of the vehicle. In an example embodiment, the vehicle speed is sensed and used as a first criteria for determining distractedness. This criterion is controlled by the driver. Other first criterion can include sensed signals related to the driver, e.g., brain waves, HR, HRV, eye movement, body position and movement and the like. These are directly controlled by the driver or produced by the driver's body. The second criterion can be traffic congestion, other vehicles speeds adjacent the vehicle, or a combination of both. The second criterion is not controlled by the driver. The second criterion may relate to vehicle or outside the vehicle data that are not under the control or produced by the driver. The relationship between the first and second criteria can indicate distractedness. For example, when the first criterion changes in a known manner and the second criterion also changes in a known manner, this indicates distractedness. A distracted driver may slow his-ther vehicle (i.e., first criterion) when surrounding traffic does not slow (i.e., second criterion). An additional first criterion can also be used to confirm distractedness, e.g., a slower and deeper breathing pattern, a change in posture, a slower heart rate, etc. In another example, a distracted driver may slow the vehicle (i.e., first criterion) and there is no slowing due to traffic congestion, other obstacle, traffic light, and the like (i.e., second criterion). This indicates possible distractedness of a driver. The controller can also take into account the operational status of the vehicle. If the vehicle is experiencing some type of operational failure, then the driver may not be distracted. The controller compares the first criterion, e.g., vehicle speed, relative to the second criterion. When the vehicle speed slows down relative to the second criterion, the controller will indicate distractedness of the driver.

The second criteria can also be relative vehicle behavior. With vehicles communicating with each other, the first criterion can be changing vehicles speeds at a first rate. The second criterion can be the rates that the vehicle speeds of other vehicles change speed relative to the changing of speed of a vehicle by the driver's being sensed. If the present vehicle changes vehicle speeds more often than the other vehicles, this indicates distractedness.

The throttle position can be sensed using a throttle position sensor. The throttle position can be used as part of the first criterion, a supplement to vehicle speed or a replacement for vehicle speed. The driver controls the position of the throttle, with the cruise control or adaptive cruise control off, which in turn controls vehicle speed.

The system may utilize adaptive tolerancing of sensing system thresholds for both the occupant and outward environmental sensing technology to improve situational distraction classification and countermeasure readiness. The external system thresholds may be influenced by the internal system indications and equally the internals system thresholds may be influenced by the external system indications.

For example, the cognitive attention measurement via the sensed electrical brain activity (e.g., EDP) may lower its distraction indication threshold if metrics such as the vehicle speed, weather, and/or lidar/radar systems indicate that the surrounding environment contains certain conditions (e.g., proximity to external objects, speed of vehicle, wet or icy road conditions) that requires higher alertness in that situation in comparison to normal operating conditions where non-distracted but also non-heightened attentions levels would not be concerning. As with the field sensing or contact based sensing of the EDP as it relates to the underlying brain activity, the internal eye and skeletal tracking sensing, autonomic nervous system monitoring, as well as the external systems and all other monitors can have multiple threshold levels both in the magnitude of their metrics (e.g. cognitive attention, eye open area, turn, HR/BR, distance, speed) and their temporal resolution (e.g. seconds per degrees of turn allowed of the head). For example, eye or skeletal tracking may indicate various degrees of turn away from the optimal viewing window of attention for various amounts of time. In situations requiring higher levels of alertness both the maximum degree of turn away from that plane and the time length allowed for each degree of turn may be lowered before an indication is given and/or a countermeasure is readied and perhaps activated.

Long term data related to detected distraction can be processed secondary to the real-time algorithms to provide a variety of statistical information for both the occupant and machine learning systems. The long-term data may be stored in the vehicle or off-vehicle on a remote server. The vehicle may include electronic communication to an external server, e.g., over WIFI, mobile communication networks, such as cellular communications, and the like. The long-term distraction calculations may be used to alter the instructions for determining distraction or for mitigating false positives. The present disclosure quantifies the distraction/concentration status of the driver while correcting for false indications of distraction. The vehicle can use the distraction/concentration status of the driver to manipulate reaction times of various vehicle safety systems, e.g., the adaptive braking system, to optimize the response of the system itself. This may reduce the risk of forward collisions.

The present system can be used in an autonomous vehicle, e.g., a levels 1-2 automobile(s), where the vehicle uses the level of distraction, a determination of distractedness, or the multiple sensor determination of a distracted driver, to be able to judge the most appropriate time to switch from manual to autonomous drive and vice-versa, or to engage certain levels of countermeasures.

This system is beneficial to all modes of transportation extending even beyond automotive and personal vehicle.

The present disclosure illustrates a controller 102. It is within the scope of the present disclosure for the controller 102 to represent multiple processors, memories and electronic control units, which can work independently with various systems to affect the functions and tasks described herein. The vehicle may use a more distributed controller system than a single controller and remain within the scope of the present disclosure. The controller 102 includes circuitry to process sensed signals that represent real world conditions and data.

The present disclosure describes the sensed EDP data to be the primary data and other data related to the person or the vehicle to be secondary data. However, some embodiments of the present disclosure use the sensed EDP as the secondary data to correct for false determinations of the distractedness based on the other non-EDP data. For example, the internal camera and the operation of the vehicle, e.g., drifting or crossing lines in the street, can be used to determine distractedness. The EDP signal can be used to validate any determination of distractedness.

A further secondary data can be time, e.g., time of day and time of vehicle usage. The vehicle may input the time of day that the vehicle is being driven as a secondary input to prevent false determinations of distractedness or alter the levels of thresholds in the cameras for determining distractedness. When the time of day is night, then the thresholds of distractedness may be lowered. The vehicle may track the usual time that the vehicle is driven in a given time period.

When the vehicle is operated outside the usual time periods, then there may be greater likelihood of distracted driving.

One example of electro-dermal potential may be a type of electroencephalography (EEG), which is an electrophysiological monitoring method to record electrical activity of the brain. It is typically noninvasive, with the electrodes placed along the scalp, although invasive electrodes are sometimes used in specific applications. EEG measures voltage fluctuations resulting from ionic current within the neurons of the brain. In clinical contexts, EEG refers to the recording of the brain's spontaneous electrical activity over a period of time, as recorded from multiple electrodes placed on the scalp. Diagnostic applications generally focus on the spectral content of EEG, that is, the type of neural oscillations that can be observed in EEG signals.

While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention.

What is claimed is:

1. A vehicle system, comprising:
an electro-dermal potential sensing system integrated into a vehicle cabin of a vehicle to sense a person and configured to output an electro-dermal potential signal;
at least one additional vehicle sensor to sense vehicle-related data and configured to output a sensor signal; and
a controller to receive the electro-dermal potential signal from the electro-dermal potential sensing system and the sensor signal from the vehicle sensor to determine a distraction state of the person using both the electro-dermal potential signal and the vehicle-related data to reduce the likelihood of a false distraction state using only one of the vehicle-related data or the electro-dermal potential signal, the controller is to output a control signal when the distraction state is determined and confirmed not false, wherein the control signal is to adjust operation of an adaptive braking system in the vehicle.

2. The vehicle system of claim 1, wherein the controller is configured to determine a false distraction state based in both the vehicle-related data and the electro-dermal potential signal.

3. The vehicle system of claim 1, further comprising a seat configured to support the person as an occupant and to be mounted in the vehicle; and wherein the electro-dermal potential sensing system includes a contactless sensor mounted in the seat adjacent a head of the occupant.

4. The vehicle system of claim 3, wherein the electro-dermal potential sensing system includes a plurality of contactless sensors mounted in the seat; and wherein the seat includes a head rest, and wherein the plurality of contactless sensors includes one or more headrest sensors mounted in the headrest to measure electro-dermal potential at a head of the driver.

5. The vehicle system of claim 3, wherein the seat includes a driver warning device to indicate to the driver that the control signal is output from the controller.

6. The vehicle system of claim 1, wherein the controller measures driver distraction based on individual frequency components in the electro-dermal potential signal.

7. The vehicle system of claim 1, wherein the controller uses the electro-dermal potential signal to determine distraction of the person and when distraction is detected outputs the control signal to increase a time to impact variable in an object avoidance calculation.

8. The vehicle system of claim 7, wherein the sensor signals include a video image output from a cabin camera to detect the person, and wherein the controller uses the video image output and the electro-dermal potential signal to determine the false distraction state of the person.

9. The vehicle system of claim 7, wherein the sensor signals include a navigational position signal from a navigational position sensor to detect position of a vehicle, and wherein the controller uses the navigational position signal and the electro-dermal potential signal to determine the false distraction state of the person.

10. The vehicle system of claim 7, wherein the sensor signals include an external camera signal from an outward facing imager to produce video external to the vehicle, and wherein the controller uses the external camera signal and the electro-dermal potential signal to determine the false distraction state of the person.

11. The vehicle system of claim 1, wherein the sensor signals include an internal video signal, an external camera signal, a navigational position signal, and a vehicle speed signal, and wherein the controller uses the internal video signal, the external camera signal, the navigational position signal, the vehicle speed signal and the electro-dermal potential signal to determine the false distraction state of the driver.

12. A vehicle system, comprising:
a vehicle safety sensor system configured to sense external objects around a vehicle and output an external sensor signal;
a seat configured to support an occupant and to be mounted in the vehicle;
an electro-dermal potential system at least partially integrated into a vehicle cabin of the vehicle and configured to output an electro-dermal potential signal; and
a controller to receive the electro-dermal potential signal from the electro-dermal potential system and the external sensor signal and to output a control signal, using the electro-dermal potential signal and the external sensor signal, to adjust operation of the vehicle safety sensor system in the vehicle.

13. The vehicle system of claim 12, wherein the electro-dermal potential system includes a plurality of contactless sensors mounted in the seat.

14. The vehicle system of claim 12, wherein the vehicle safety sensor system includes a detection and ranging system with a range setting to sense objects outside including a position and a range of an external object and the external sensor signal includes the position and range of the external object.

15. The vehicle system of claim 14, wherein the controller outputs a range extension signal when the controller determines that the driver is distracted using the electro-dermal potential signal, and wherein the vehicle safety sensor system extends the range setting when the controller outputs the range extension signal.

16. The vehicle system of claim 12, further comprising a collision avoidance system having a trigger time based on the control signal from the controller, and wherein the collision avoidance system triggers an avoidance action based on the trigger time.

17. The vehicle system of claim 16, wherein the collision avoidance system has a first trigger time when distraction is not detected and a second trigger time when distraction is detected, the second trigger time being less than the first trigger time.

18. A vehicle system, comprising:
- an electro-dermal potential sensing system integrated into a vehicle cabin of a vehicle to sense a person and configured to output an electro-dermal potential signal;
- at least one additional vehicle sensor to sense vehicle-related data and configured to output a sensor signal; and
- a controller to receive the electro-dermal potential signal from the electro-dermal potential sensing system and the sensor signal from the vehicle sensor to determine a distraction state of the person using both the electro-dermal potential signal and the vehicle-related data to reduce the likelihood of a false distraction state using only one of the vehicle-related data or the electro-dermal potential signal, the controller is to output a control signal when the distraction state is determined and confirmed not false;
- wherein the controller uses the electro-dermal potential signal to determine distraction of the person and when distraction is detected outputs the control signal to increase a time to impact variable in an object avoidance calculation.

19. The vehicle system of claim 18, wherein the controller is configured to determine a false distraction state based in both the vehicle-related data and the electro-dermal potential signal.

20. The vehicle system of claim 19, wherein the control signal is to adjust operation of an adaptive braking system in the vehicle.

* * * * *